(12) United States Patent
Takahashi et al.

(10) Patent No.: US 7,718,438 B2
(45) Date of Patent: May 18, 2010

(54) METHOD FOR PRODUCING A MICROARRAY

(75) Inventors: Atsushi Takahashi, Hiroshima (JP); Takashi Akita, Hiroshima (JP); Chiho Itou, Hiroshima (JP); Haruko Miyauchi, Hiroshima (JP); Kei Murase, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 808 days.

(21) Appl. No.: 10/297,936

(22) PCT Filed: Jun. 20, 2001

(86) PCT No.: PCT/JP01/05274

§ 371 (c)(1),
(2), (4) Date: Dec. 20, 2002

(87) PCT Pub. No.: WO01/98781

PCT Pub. Date: Dec. 27, 2001

(65) Prior Publication Data

US 2005/0063877 A1 Mar. 24, 2005

(30) Foreign Application Priority Data

Jun. 20, 2000 (JP) ............................. 2000-184393

(51) Int. Cl.
*G01N 33/48* (2006.01)
(52) U.S. Cl. ..................... 436/94; 435/6; 435/287.2
(58) Field of Classification Search .................. 436/94; 435/6, 287.2
See application file for complete search history.

(56) References Cited

U.S. PATENT DOCUMENTS

| 5,700,637 | A | 12/1997 | Southern |
| 6,037,186 | A | 3/2000 | Stimpson |
| 6,054,270 | A | 4/2000 | Southern |
| 6,129,896 | A | 10/2000 | Noonan et al. |
| 6,235,473 | B1 * | 5/2001 | Friedman et al. ............... 435/6 |
| 6,713,309 | B1 | 3/2004 | Anderson et al. |
| 7,122,378 | B1 * | 10/2006 | Akita et al. ................... 436/94 |

FOREIGN PATENT DOCUMENTS

| EP | 0 671 622 A1 | 9/1995 |
| JP | 7-120397 | 5/1995 |
| JP | 11-108928 | 4/1999 |
| JP | 11-211653 | 8/1999 |
| WO | WO 98/55231 | 12/1998 |
| WO | WO 99/13313 | 3/1999 |
| WO | WO 99/19711 | 4/1999 |

OTHER PUBLICATIONS

Southern et al., "Molecular Interactions on Microarrays," Nature Genetics, vol. 21 supplement pp. 5-9 (10 pp.), 1999.
Dubiley et al., "Fractionation, Phosphorylation and Ligation on Oligonucleotide Microchips to Enhance Sequencing by Hybridization", Oxford Journals Online, Oxford University Press 1997, pp. 2259-2265 (12 pp.).
Yershov et al., "DNA Analysis and Diagnostics on Oligonucleotide Microchips", PNAS, vol. 93, May 1996, pp. 4913-4918 (6 pp.).
Righetti et al., "Laterally Aggregated' Polyacrylamide Gels for Electrophoresis", Electrophoresis, 1992, vol. 13, pp. 587-595 (9 pp.).
Dave et al., "Sol-Gel Encapsulation Methods for Biosensors", Analytical Chemistry, vol. 66. No. 22, Nov. 15, 1994, pp. 1120-1179 (11 pp.).

* cited by examiner

*Primary Examiner*—Lyle A Alexander
(74) *Attorney, Agent, or Firm*—Oblon, Spivak, McClelland, Maier & Neustadt, L.L.P.

(57) ABSTRACT

A microarray obtainable by slicing a block comprising a plurality of linear bodies or through-holes which carry an organism-related substance, in a direction intersecting the longitudinal direction of the linear bodies or through-holes, wherein the linear body and/or block comprise a substance that reduces the self-fluorescence thereof.

7 Claims, 1 Drawing Sheet

100 7,718,438 B2

METHOD FOR PRODUCING A MICROARRAY

FIELD OF THE INVENTION

The present invention relates to a microarray on which an organism-related substance is immobilized as a probe, which can be used in fields such as clinical testing and food product testing, and to a method of producing the same.

BACKGROUND OF THE INVENTION

Recently, new analysis methods and methodologies known as DNA microarray methods (DNA chip methods) which allow one-operation expression analysis of numerous genes, have been developed and now attract attention. These methods do not differ in principle from conventional methods in respect of the fact that they are nucleic acid detection and quantification methods based on nucleic acid-nucleic acid hybridization. However, a major characteristic of these methods is the utilization of a microarray or chip which comprises a large number of DNA fragments aligned and immobilized at high density on a flat substrate. Examples of a specific method of using a microarray method include hybridizing a sample of expression genes of a test subject cell labeled with fluorescent pigment on a flat substrate slice, allowing mutually complimentary nucleic acids (DNA or RNA) to bind with one another and after labeling these locations with fluorescent pigment, rapidly reading with a high resolution analysis device. In this way, respective gene amounts in a sample can be rapidly estimated. That is, the introduction of these new methods has enabled a reduction in reaction sample amount, and high volume, rapid, systematic analysis and quantification of these reaction samples with good reproducibility.

As methods of producing these DNA microarrays, there have been disclosed a method wherein DNA is compartmentalized and immobilized on a glass substrate, and a method wherein nucleic acids are synthesized one by one on compartmentalized regions on a silicon substrate using photolithography techniques used in the production of semiconductor chips (U.S. Pat. No. 5,445,934; U.S. Pat. No. 5,774,305).

Further, there have been disclosed a method of a obtaining a DNA microarray wherein DNA is immobilized on linear bodies comprising glass or high molecules, and these linear bodies are sheet-rolled together with adhesive, and sliced in the direction of the cross-section of the fiber (Japanese Patent Publication (Unexamined Application) No. 11-108928); a method of obtaining a DNA microarray wherein a plurality of fibers have DNA etc. immobilized thereon, these are bundled together and this bundle is sliced across the longitudinal direction of the fibers DNA microarray (Japanese Patent Publication (Unexamined Application) No. 2000-245461); and further a method of obtaining a DNA microarray wherein a plurality of through-holes are made in a resin block, and after the these holes are made to carry DNA etc., the block is sliced (Japanese Patent Publication (Unexamined Application) No. 2000-78998). Because these methods of production allow a plurality of microarrays to be prepared by repeated slicing, they are particularly preferable methods for mass producing chips having the same sequences.

For example, in general, detection of specific DNA within an analyte using the DNA microarrays exemplified above, is performed by fluorescence-labeling probe DNA immobilized on the chip, or analyte DNA, irradiating the probe or analyte which has formed a hybrid due to performing operations such as hybridization etc., with fluorescence excitation light from an external source, and detecting fluorescence excitation emitted from the fluorescent molecules.

However, when detecting an organism-related substance such as DNA which is contained in an analyte in only trace amounts, fluorescence other than that emitted from the probe or analyte, specifically, self-fluorescence of the substrate etc., carrying the probe, is detected as noise, and there was the problem that trace amounts of an organism-related substance could not be detected.

Further, a method of producing a plurality of microarrays by repeated slicing is superior in respect of the fact that a large amount of microarrays having the same arrangement can be mass produced. However, there is the problem that curvature of the microarray occurs.

DISCLOSURE OF THE INVENTION

The present invention is directed to providing a microarray which reduces the noise light emitted from other than the probe or analyte, and enables detection of trace components. Further, the present invention is directed to providing a method of producing a plurality of microarrays by repeated slicing, wherein microarrays are produced efficiently without defects such as curvature.

The present inventors, as a result of deliberate study directed to solving the above problems, discovered addition of a substance which reduces self-fluorescence to a material constituting a microarray enables detection of trace amounts of analytes. Further, the present inventors discovered that addition of a substance which reduces self-fluorescence to a material constituting a microarray in the method of producing this microarray enabled efficient production of a microarray without defects such as curvature.

That is to say, the present invention is as follows:

1. A microarray obtainable by slicing a block comprising a plurality of linear bodies or through-holes which carry an organism-related substance in a direction intersecting the longitudinal direction of the linear bodies or through-holes, wherein the linear bodies and/or block comprise a substance that reduces the self-fluorescence thereof.
2. A method of producing a microarray which comprises forming a plurality of through-holes in a block which comprises a substance that reduces self-fluorescence of the block, allowing the through-holes to carry an organism-related substance and slicing the block in a direction intersecting the longitudinal direction of the through-holes.
3. A method of producing a microarray which comprises preparing a block by immobilizing a bundle of linear bodies carrying an organism-related substance with a resin comprising a substance that reduces self-fluorescence; and slicing the block in a direction intersecting the longitudinal direction of the linear bodies.
4. A method of producing a microarray which comprises preparing a block by immobilizing a bundle of linear bodies with a resin comprising a substance that reduces self-fluorescence, and after allowing each of the linear bodies to carry an organism-related substance, slicing the block in a direction intersecting the longitudinal direction of the linear bodies.
5. The methods of 3 or 4 above wherein the linear body comprises the substance that reduces self-fluorescence.

In the above microarray or method of producing the above microarray, examples of linear bodies include fibers such as hollow fibers, and examples of a block includes one comprising resin. Further, examples of a substance that reduces self-fluorescence include an absorbent (e.g. an inorganic pigment) and/or a quencher.

The inorganic pigment is preferably carbon black, and the content thereof is, for example, 0.5 to 10% by mass.

The present invention is explained in detail below. The content of the specification and/or drawings of Japanese Patent Application No. 2000-184393 which forms the basis of a claim to priority in the present application, is incorporated herein.

In the present invention, an example of a organism-related substance is one selected from the group consisting of the following (1) to (3):

(1) a nucleic acid, amino acid, saccharide or lipid
(2) a polymeric substance comprising at least one of the types of the substances in (1) above
(3) a substance that interacts with the above substance (1) or (2)

For example, where nucleic acid is used as an organism-related substance, preparation of DNA or RNA from cells can be performed by known methods. For example, DNA extraction can be performed according to the method of Blin et al. (Nucleic Acids Res.3.2303 (1976)), etc., and RNA extraction can be performed by the method of Favaloro et al. (Methods.Enzymol.65.718 (1980)), etc. Further, linear or circular plasmid DNA or chromosomal DNA can be used. As DNA, DNA fragments that have been cleaved chemically or by restriction enzymes, DNA synthesized by enzymes, etc. in vitro, or chemically synthesized oligonucleotides, etc. can be used.

In the present invention, a block consists of linear bodies or through-holes, and a block body excluding these linear bodies or through-holes. That is, a block may consist of a block body and linear bodies carried therein. Or, another block may consist of a block body and through-holes formed therein.

For a material for the block body, a known resin composition such as a polyamide, polyester, acryl, polyurethane, phenol, fluorine resin composition is used.

In the present invention, linear bodies or through-holes provide a place for carrying the organism-related substance. These linear bodies or through-holes have an substantially linear construction, and the linear bodies or through-holes are each arranged so to be substantially parallel to one another. The shape of the cross-section of the linear bodies or through-holes may be of any shape. The most preferable shape of a cross-section is circular. Normally, a plurality of linear bodies or through-holes are arranged.

The arrangement density of the linear bodies or through-holes is not particularly limited, and where a large amount of data is to be obtained in a single analysis, it is preferable to arrange around linear bodies or through-holes at a density of 100 to 1,000,000/cm$^2$ on a single microarray. Further, the linear bodies are preferably arranged such that there are equal intervals between neighboring linear bodies.

A linear body is constituted by for example, a solid fiber, a porous solid fiber, a metal wire, a hollow fiber, a porous hollow fiber, or glass tube, etc. Further, after bundling of a plurality of fine linear bodies, these may be twisted so that the whole becomes a single linear body.

Organism-related substances of different types can be carried by each of the individual through-holes or linear bodies. Or, the same type of organism-related substance can be carried by a plurality of through-holes or linear bodies.

In the present invention, a linear body and/or block comprises a substance that reduces the self-fluorescence that originates from the linear body and/or block. Examples of such a substance include, a substance which absorbs self-fluorescence (absorbent) and a substance (quencher) which causes de-excitation of self-fluorescence.

Examples of absorbents include organic and inorganic pigments. Specifically, black pigments include carbon black, acetylene black and iron black; yellow pigments include chrome yellow, zinc yellow, ocher, Hansa Yellow, permanent yellow, and benzine yellow; orange pigments include orange lake, molybdenum orange and benzine orange; red pigments include bengara, cadmium red, antimony vermilion, permanent red, lithol red, lake red, brilliant scarlet and thio-indigo red; blue pigments include ultramarine, cobalt blue, copper phthalocynanine blue and indigo; and green pigments include, chrome green, viridian naphtol green and copper phthalocyanine green.

In particular, the attenuation of self-fluorescence intensity by an absorbent is dependent on the number and frequency of collisions between fluorescence light waves and the absorbent within the linear body and/or block body and, distance which the fluorescent light waves. Therefore, to maximize the effect of the absorbent, it is preferable to use absorbents having particles that are as small as possible, and that these are uniformly dispersed. Carbon black is particularly preferable as such an absorbent.

As absorbents, absorbents that can reduce self-fluorescence, and which, at the time of detection, do not interfere with the fluorescence of the fluorescent substance to be detected, are selected. For example, where a substance bound to fluorescein isothiocyanate (FITC) is to be detected, a pigment other than a yellow or green pigment is selected.

In cases where a plurality of fluorescent labels are used such as in a dual fluorescent detection method, it is preferable to select an absorbent that can absorb light over a broad range of the visual light region. An example of such an absorbent is a black pigment.

Examples of a quencher include paramagnetic ions such as Fe(III), Ni(II), Cr(III), Cu(II) and Ti(I). Further examples include molecules not possessing an electric charge such as acrylamide, etc.

Regarding the above described absorbent and/or quencher, normally either an absorbent or a quencher is used, but it is also possible to use both in combination.

Further, in the present invention, as required, some or all of the linear bodies can be stained. By staining some or all of the linear bodies, stained linear bodies can be used as coordinate standards when detecting an analyte.

The thickness of the microarray according to the present invention is preferably 5 mm or less (for example, 50 μm to 5 mm) and more preferably 1 mm or less (e.g. 100 μm to 1 mm).

Examples of methods of producing microarrays using the above materials are described below.

An organism-related substance is physically or chemically carried on an outer surface, on an inner wall part of a hollow part, or in a porous part of a linear body. Further an organism-related substance is physically or chemically carried in a hollow part or on an inner wall part of a through-hole. The method of carrying the organism-related substance, the type of organism-related substance to be carried, and the material and shape of the linear body or through-hole, are selected as appropriate. For example, an linear body can be made to carry an organism-related substance by soaking the linear body in a solution containing the organism-related substance followed by baking or irradiating with ultraviolet. Further, if the linear body is a hollow fiber, the fiber can be made to carry an organism-related substance by a method which involves treating the inner wall of the hollow part can be treated with a suitable coating agent such as poly-L-lysine, and introducing the organism-related substance to the hollow portion, or which involves filling the hollow portion with a high molecular polymer such as an acrylide polymer or agarose including an organism-related substance.

Methods for immobilizing a bundle of linear bodies in a block body include for example a method of immobilizing a bundle which involves arranging and immobilizing a plurality of linear bodies in parallel on a sheet such as an adhesive sheet, rolling the sheet in a spiral form and pouring resin, etc. into aperture parts of the roll; and a method of immobilizing a bundle which involves overlapping 2 perforated boards having a plurality of hole, allowing a linear body to pass through each of the holes present in these perforated boards, opening an interval between the 2 perforated boards, and pouring resin, etc. into this interval.

Methods of forming a plurality of through-holes within a block body include a method which involves preparing a block body that comprises resin, etc., and forming through-holes in the block body by using a drill or laser, etc.; and a method of which involves preparing a block incorporating a plurality of metal wires, and forming through-holes by pulling the metal wires out from the block.

A method of incorporating substance that reduces self-fluorescence in a linear body involves, for example, where a fiber is used as a linear body, dispersing and incorporating the absorbent and/or quencher within the fiber by spinning the fiber in a state where the absorbent and/or quencher has already been mixed into the fiber raw material.

Further, examples of methods of incorporating the substance that reduces self-fluorescence into the block body include a method of incorporating an absorbent and/or quencher at the time of the formation process of the block body.

Microarrays can be produced by slicing the thus obtained block comprising a plurality of linear bodies or through-holes which carry an organism-related substance, in a direction intersecting the longitudinal direction of the linear bodies or through-holes. The angle of slicing is not particularly limited but it is preferable for the purpose of allowing full use of the organism-related substances carried in a thick portion when detecting an analyte, to slice in a direction perpendicularly intersecting the longitudinal direction of the linear bodies or through-holes.

In the method of producing according to the present invention, useful effects at the time of slicing are provided by adding a substance that reduces self-fluorescence preferably an inorganic pigment, or more preferably carbon black, to a linear body and/or block.

For example, because in resin having carbon black uniformly dispersed therein, carbon black behaves as a pseudo crosslinking point, such resin becomes harder than resin hardened under identical hardening conditions. Thus it becomes possible to control distortion of the resin, distortion of the linear bodies contained in the resin, and curvature of the microarrays at the time of slicing. Because the above effect becomes more prominent the thinner the thickness of the microarray, the method of the present invention is a suitable method for producing microarrays having a thickness of 1 mm or lower, preferably 500 µm or lower (100 to 500 µm).

Further, where carbon black is used, viscosity of the linear body and/or block is reduced and further, static electricity can be reduced. Therefore, when repeatedly slicing a block, cohesiveness between microarrays etc. can be prevented. Further, adsorption at the time of production or detection of dust, or microorganisms or spores floating in the air can be prevented.

When carbon black is dispersed in a linear body, the linear body becomes black colored. Therefore, because visibility is improved when the linear bodies are bundled, arrangement operations become simpler.

Further, in the case where a hollow portion of the linear body or a through-hole carries the organism-related substance by means of a gel, because there is roughening of an inner wall surface of a linear body, or a through-hole-facing surface of a block body to which an inorganic pigment has been added, cohesion with the gel improves. Thus, it is possible to prevent defluxion of the gel from the microarray at the time of slicing.

To obtain an effect such as the one described above, it is preferable for the inorganic pigment to be fully dispersed throughout the linear body and/or block. Further, addition of a large amount is preferable for thorough reduction of self-fluorescence originating from the linear body and/or block and addition of a small amount is preferable for good dispersion through the linear body and/or block. If the pigment is carbon black, the amount thereof to be added is preferably 0.5-10% by mass relative to the linear body and/or block.

BEST MODE FOR WORKING THE INVENTION

Figure 1:
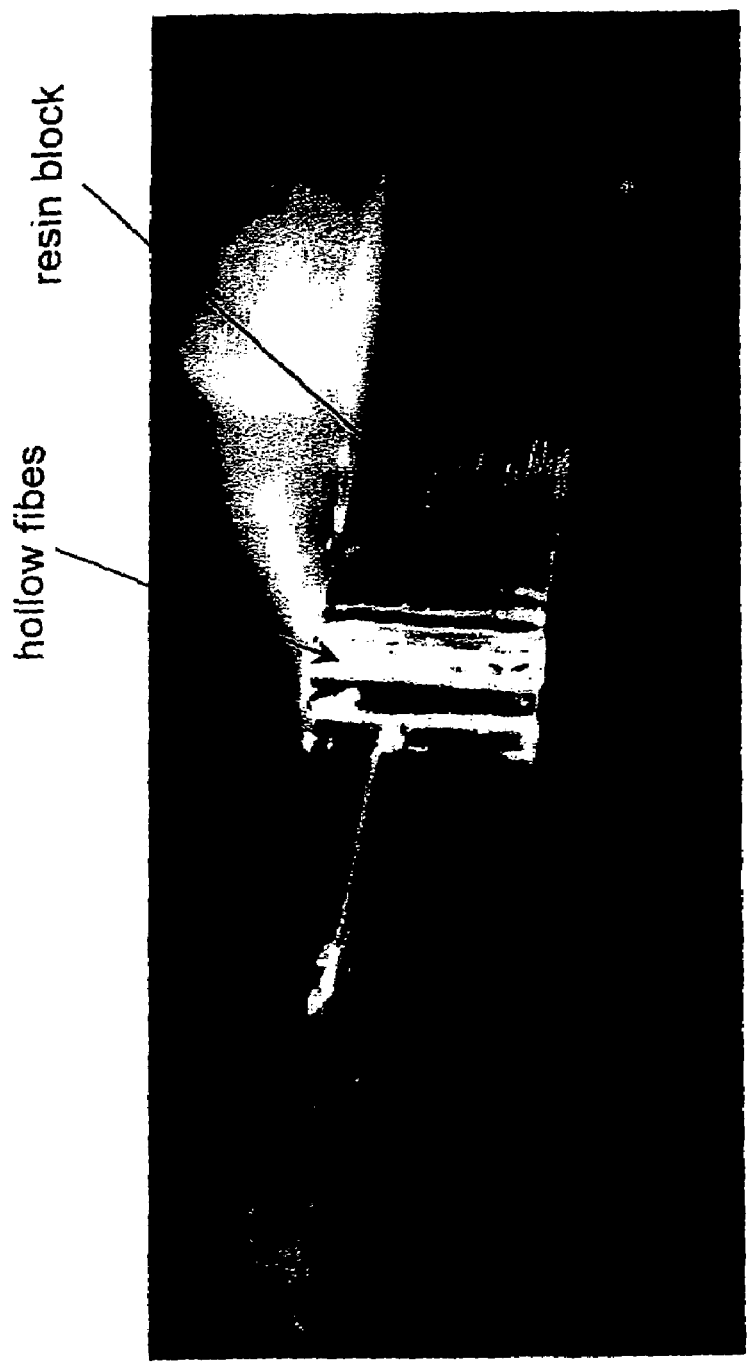
FIG. 1 is a photograph showing a microarray (cross-sectional view) sliced from a resin block to a thickness of 500 µm.

The present invention is explained below in more detail by way of Examples. However, the technical scope of the present invention is not limited by these Examples.

EXAMPLE 1

Two strands of piano wire (length, 10 cm) having a diameter of 2 mm were arranged in parallel, and a resin block was prepared such that it comprised these piano wires. As resin, polyurethane resin adhesive (Nippon Polyurethane Industry Co., Ltd. nippolan4276, coronate4403) was used. First, relative to the total weight of nippolan4276/coronate4403 with a formulation ratio of 62/38, 0.5% by mass, 1.0% by mass or 2.5% by mass, carbon black (MA-100 manufactured by Mitsubishi Chemical Corporation) was added to nippolan4276, respectively, and dispersed using a homogenizer for 3 hours. Next, coronate4403 was added, and the mixture allowed to harden at room temperature for about 1 week. A 2 cm×2 cm×7 cm carbon black-dispersed polyurethane block comprising piano wires was prepared. Next, by pulling out the piano wire, two through-holes having a length of 7 cm were formed within the block.

The obtained block was sliced with a microtome in a direction perpendicular to the longitudinal direction of the through-holes, to obtain 10 slices having a thickness of approximately 500 µm. There was no curvature in any of the slices. Further, carbon black had fully dispersed within the block.

Three slices where arbitrarily selected from among the obtained slices, and observed with Nikon fluorescent microscope E600/Hamamatsu Photonicks chilled CCD camera C488-37. Detection fluorescent intensity of the slices was measured by exposure for 30 seconds using Cy3 filter (incident light side: 535±25 nm, detection light side: 610±75 nm). After measurement, the average value of the fluorescent intensity of the 3 slices was determined. Results are shown in Table 1.

TABLE 1

| Carbon black concentration (% by mass) | Fluorescent intensity |
|---|---|
| 0.5 | 5462 |
| 1 | 5157 |
| 2.5 | 4919 |

EXAMPLE 2

(1) Preparation of Hollow Fiber Alignment

Two perforated boards having a total of 49 holes (7×7, horizontally and vertically) with a diameter of 0.32 mm, and a center distance of 0.42 mm were overlapped, and 49 polyethylene hollow fibers (outer diameter: 0.3 mm, inner diameter: 0.2 mm) were passed through respective holes in both of these boards. An interval of 50 mm was created between both boards, and with the fibers in a stretched state, both ends were immobilized. As in Example 1, 2.5% by mass of carbon black relative to the total weight of polyurethane resin adhesive was added and mixed. This resin raw material was poured to surround the hollow fiber alignment and allowed to harden. Next, by removing the perforated boards, a resin block incorporating hollow fibers was obtained.

(2) Preparation of a Fluorescence Labeled Oligonucleotide Having a Methacrylate Group Synthesis of oligonucleotides was performed by using PE Biosystems automated synthesizer DNA/RNA synthesizer (model 394). An oligonucleotide with the sequence GCAT with Cy3 introduced to the 5'-terminal in the final step of DNA synthesis, was synthesized (Cy3-GCAT). These were deprotected and purified for use according to general methods.

Fifty microliters of the obtained Cy3-GCAT (500 nmol/ml), 5 µl of glycidyl methacrylate and 5 µl of dimethyl formamide (DMF) were mixed, and allowed to react at 70° C. for 2 hours to prepare a fluorescent pigment having a methacrylate group. To this, 190 µl of water was added, and 100 nmol/ml of a fluorescent pigment (GMA-modified Cy3-GCAT) having a methacrylate group was obtained.

(3) Preparation of a Fiber Alignment and Slice Thereof Carrying a Gel with Nucleic Acid Immobilized Therein A monomer solution and initiator solution were prepared by mixing according to the following relative masses.

| (a) Monomer solution | |
|---|---|
| Acrylamide | 0.76 parts by mass |
| Methylene bis-acrylamide | 0.04 parts by mass |
| Water | 4.2 parts by mass |
| (b) Initiator solution | |
| 2,2'-azo bis(2-amidinopropane) dihydrochloride | 0.01 parts by mass |
| Water | 4.99 parts by mass |

GMA-modified Cy3-GCAT prepared according to (2) above was admixed to the monomer solution (a) and initiator solution (b) to achieve concentrations shown in Table 2. (Polymer solution 1 to 5).

Hollow portions of the hollow fibers in the resin block obtained in (1) were filled with the obtained polymer solution, a polymerization reaction was performed by transferring the block to a sealed glass container saturated with water vapor and allowing to stand for 4 hours at 80° C.

TABLE 2

| | Polymer solution 1 | Polymer solution 2 | Polymer solution 3 | Polymer solution 4 | Polymer solution 5 |
|---|---|---|---|---|---|
| Cy3 concentration (nmol/L) | 0.5 | 0.05 | 0.005 | 0.0005 | 0.00005 |
| Cy3 amount (pmol)/1 spot | 10 | 1 | 0.1 | 0.01 | 0.001 |

After completion of the polymerization reaction, the block was sliced repeatedly in a direction perpendicular to the longitudinal direction of the hollow fibers using a microtome, to obtain 30 slices of a thickness of approximately 750 µm. There was no curvature in any of the obtained slices. Further, carbon black had fully dispersed within the block.

Three slices where arbitrarily selected from among the obtained slices, and observed with Nikon fluorescent microscope E600/Hamamatsu Hotnicks chilled CCD camera C488-37. Measurement of the detection light intensity of the microarray was performed using a filter similar to that used in Example 1, and thereafter the average value of the fluorescent intensity of the 3 slices was determined. As a result, detection was possible to 0.005 nmol/L of Cy3.

COMPARATIVE EXAMPLE 1

With the exception that carbon black was not admixed, a slice was prepared by a method similar to that of Example 2, and the fluorescence intensity of the obtained slice was measured. As a result, detection was impossible at 0.005 nmol/L of Cy3, and detection was not possible up to 0.05 nmol/L of Cy3.

TABLE 3

| | Relative fluorescent intensity | |
|---|---|---|
| | Example 2 | Comparative Example 2 |
| Polymer solution 5 | 1.00 | N.T. |
| Polymer solution 4 | 1.01 | 1.07 |
| Polymer solution 3 | 1.86 | 1.00 |
| Polymer solution 2 | 9.12 | 5.48 |
| Polymer solution 1 | N.T. | 74.5 |

N.T. = not tested

Relative fluorescent intensity was calculated by establishing the fluorescent intensity of polymer solution 5 in Example 2, and polymer solution 3 in the comparative example, as 1.

EXAMPLE 3

A resin block was prepared as per Example 2, except that instead of polyethylene hollow fibers, polymethyl methacrylate (PMMA) hollow fibers (outer diameter 0.3 mm, inner diameter 0.2 mm) comprising 1.6 parts by mass carbon black was used. After 10 days, hardness of the resin block was measured 5 seconds after a pressure applying surface was applied to the resin block according to JIS K 7215. As a result, hardness was 95. Thirty slices were obtained by slicing the block. There was no curvature in any of the slices.

COMPARATIVE EXAMPLE 2

In Example 3, a resin block was prepared without adding carbon black to the hollow fiber and resin. After 10 days, hardness of the resin block was measured according to JIS K 7215, and was 72. When this resin block was sliced at a thickness of 500 μm, the obtained slices were each slices having curvature (See FIG. 1).

All publication patents and patent applications cited in the present invention are incorporated by reference in their entirety into the present invention.

INDUSTRIAL APPLICABILITY

The present invention provides a microarray and a method of producing the same. By addition of a substance that reduces self-fluorescence to the linear body and/or block, it is possible to dramatically reduce background and cross-talk at the time of detection, and thus improve detection sensitivity. Further, by adding a substance that reduces self-fluorescence to a linear body and/or block it is possible at the time of production to stably produce a microarray that does not have curvature etc., during slicing.

The invention claimed is:

1. A method of producing a microarray which comprises:
   forming a block which comprises carbon black, fully dispersed throughout the block, that increases a hardness of the block;
   after the forming the block, forming a plurality of through-holes in the block via a drill or a laser;
   allowing the through-holes to carry a biological substance;
   allowing the block to harden; and
   slicing the block in a direction intersecting the longitudinal direction of the through-holes, wherein
   the biological substance is selected from a group including
   (a) a nucleic acid, an amino acid, a saccharide, or a lipid,
   (b) a polymeric substance including at least one substance in (a), and
   (c) a substance that interacts with a substance in (a) or (b).

2. A method of producing a microarray which comprises:
   preparing a block by overlapping perforated boards having a plurality of holes, passing linear bodies carrying a biological substance through each of the plurality of holes in the perforated boards, opening an interval between the perforated boards, and pouring a resin into the interval to immobilize the linear bodies, the resin comprising carbon black fully dispersed throughout the resin, wherein the carbon black increases a hardness of the resin;
   allowing the block including the resin to harden; and
   slicing the block in a direction intersecting the longitudinal direction of the linear bodies, wherein
   the biological substance is selected from a group including
   (a) a nucleic acid, an amino acid, a saccharide, or a lipid,
   (b) a polymeric substance including at least one substance in (a), and
   (c) a substance that interacts with a substance in (a) or (b).

3. A method of producing a microarray which comprises:
   preparing a block by overlapping perforated boards having a plurality of holes, passing linear bodies through each of the plurality of holes in the perforated boards, opening an interval between the perforated boards, and pouring a resin into the interval to immobilize the linear bodies, the resin comprising carbon black fully dispersed throughout the resin, wherein the carbon black increases a hardness of the resin;
   allowing each of the linear bodies to carry a biological substance,
   allowing the block including the resin to harden; and
   slicing the block in a direction intersecting the longitudinal direction of the linear bodies, wherein
   the biological substance is selected from a group including
   (a) a nucleic acid, an amino acid, a saccharide, or a lipid,
   (b) a polymeric substance including at least one substance in (a), and
   (c) a substance that interacts with a substance in (a) or (b).

4. The method of producing as in claim 2, wherein the allowing the through-holes to carry the biological substance includes carrying the biological substance via a gel.

5. The method of producing as in claim 2, further comprising:
   soaking a bundle of linear bodies with a biological substance; and
   baking the bundle of linear bodies with an ultraviolet light.

6. The method of producing as in claim 3, wherein
   the linear bodies are hollow fibers, and
   the allowing each of the linear bodies to carry the biological substance includes introducing the biological substance to a hollow part of the hollow fibers by filling the hollow part with a high molecular polymer including the biological substance.

7. The method of production as in any one of claims 1-3, wherein the carbon black content is 0.5-10% by mass.

* * * * *